(12) United States Patent
Lykken et al.

(10) Patent No.: US 6,674,072 B2
(45) Date of Patent: Jan. 6, 2004

(54) PREPARATION OF THIN LEAD SAMPLES FOR ALPHA PARTICLE EMISSION TEST

(75) Inventors: Glenn I. Lykken, Grand Forks, ND (US); Berislav Momcilovic, Grand Forks, ND (US)

(73) Assignee: University of North Dakota, Grand Forks, ND (US)

( * ) Notice: Subject to any disclaimer, the term of this patent is extended or adjusted under 35 U.S.C. 154(b) by 194 days.

(21) Appl. No.: 10/001,222

(22) Filed: Nov. 15, 2001

(65) Prior Publication Data

US 2003/0094571 A1 May 22, 2003

(51) Int. Cl.$^7$ .............................................. G01N 31/00
(52) U.S. Cl. ...................................................... 250/304
(58) Field of Search ........................ 250/304; 438/614, 438/613; 257/781, 779, 772

(56) References Cited

U.S. PATENT DOCUMENTS

| | | | |
|---|---|---|---|
| 4,584,161 A | 4/1986 | Post, Jr. et al. | 376/143 |
| 6,346,469 B1 * | 2/2002 | Greer | 438/614 |

OTHER PUBLICATIONS

Bauman, Robert, et al., Call for Improved Ultra–Low Background Alpha–Particle Emission Metrology for the Semiconductor Industry, Technology Transfer 190 01054118A–XFR, International Sematech, May 15, 2001.
Lykken, G., et al., Clean Galena, Contaminated Lead, and Soft Errors in Memory Chips, Journal of Electronic Materials, vol. 29, No. 10, 2000, pp. 1290–1293.
Scientific American, Bad Connections, Deleading Solder Creates Worries About Electronics Reliability, Dec. 1999, pp. 50, 54.
Young, Patrick, Technologies of the Next Century, The Industrial Physicist, Dec. 1999, pp. 14–15.
Brodzinski, Ron, A White Paper on Alpha Activity in Lead, Summer 1998.
Zastawny, Andrzej, et al., Changes in the Surfaces Radioactivity of Lead–the Effect of the Diffusion of Bismuth and Polonium Radioisotopes, Appl. Radiat. Isot. vol. 40, No. 1, pp. 19–25, 1989.
Bouldin, D. P., The Measurement of Alpha Particle Emissions from Semiconductor Memory Materials, Journal of Electronic Materials, vol. 10, No. 4, 1981, pp. 747–795.
Lantz, Leon II, Tutorial: Soft Errors Induced by Alpha Particles, IEEE Transactions on Reliability, vol. 45, No. 2, 1996.
May, Timothy C., Alpha–Particle–Induced Soft Errors in Dynamic Memories, IEEE, pp. 2–9.

* cited by examiner

Primary Examiner—Kiet T. Nguyen
(74) Attorney, Agent, or Firm—Kinney & Lange, PA

(57) ABSTRACT

A method of preparing a lead sample to determine an amount of alpha particle emission. First, a thin slice is obtained from the lead source, such as by cutting the lead source using a microtome. The thin slice may be rolled to flatten any wrinkles caused by the cutting. The flattened slice is then heated to near the melting point of lead to drive the polonium atoms to the surface of the slice. The slice may be cooled down to ambient temperature in Nitrogen gas. Once so prepared, the thin slice can be tested for an amount of alpha particle emission.

31 Claims, 3 Drawing Sheets

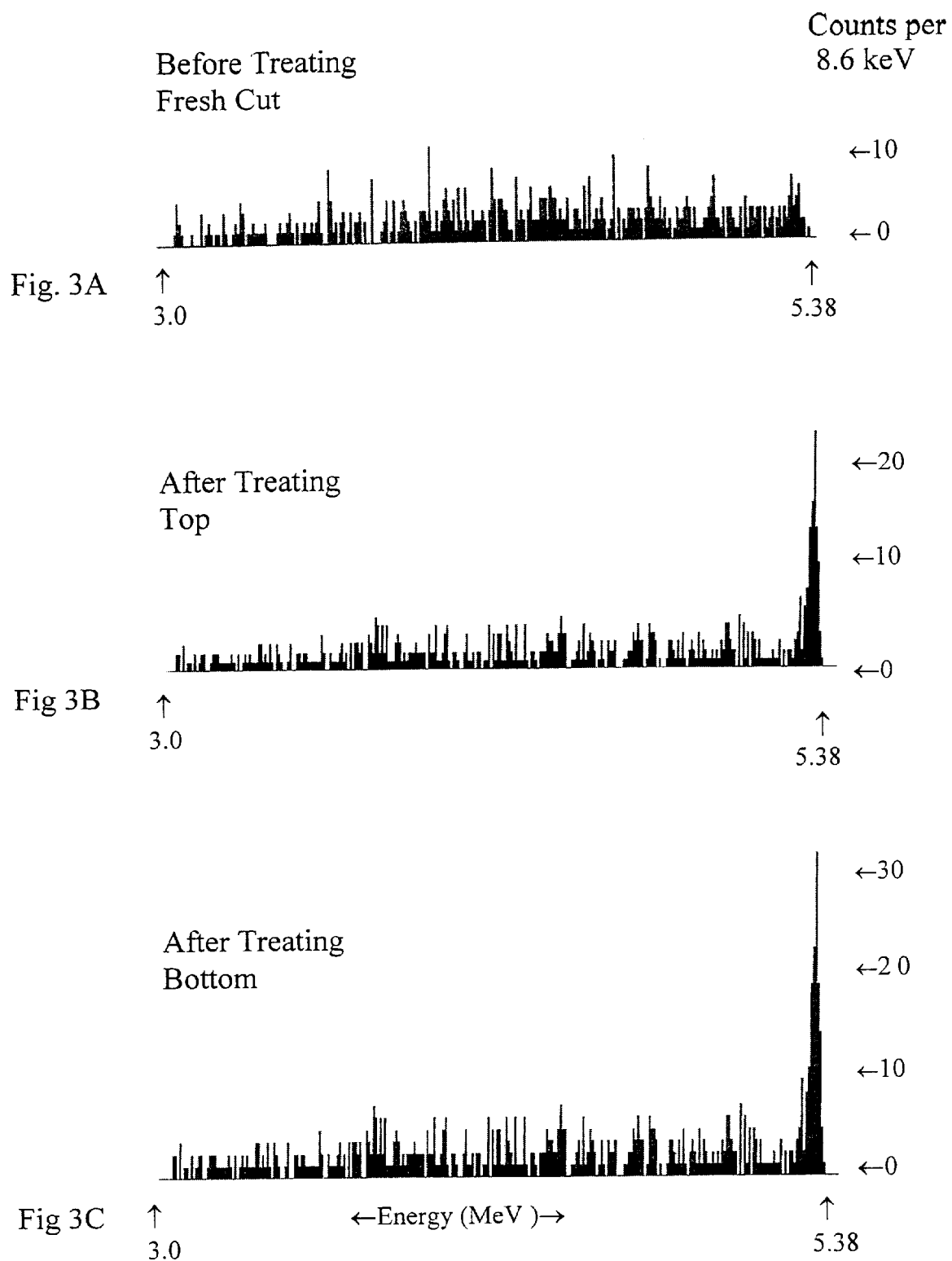

PREPARATION OF THIN LEAD SAMPLES FOR ALPHA PARTICLE EMISSION TEST

CROSS-REFERENCE TO RELATED APPLICATION(S)

None.

BACKGROUND OF THE INVENTION

The present invention is a method for preparing thin lead samples to test for emission levels of naturally occurring radioactive contaminants, such as polonium.

Lead has a variety of uses in the electronics industry, and is commonly used to make electrical contacts in high density high memory computer chips. In particular, lead is a major component in the solder used to form many of the connections and contacts required in computer chips and circuits. These solder connections are typically in the form of small spheres, or solder bumps, approximately two thousands of an inch in diameter.

Memory chips are based on binary logic and typically consist of small solid state capacitors with potential wells that are either filled with electrons (0) or not filled (1). A "soft error" is said to occur when an empty well (1) is changed to a filled well (0). Such soft errors may occur when ionizing radiation from the lead solder passes through the substrate of the chip, which is often formed of silicon, and releases electrons from covalent bonds. These free electrons collect under the positive electrode, and thereby fill the normally empty potential well. A main source of the ionizing radiation which can cause soft errors is alpha particle emission from polonium-210, a radioactive daughter of lead-210 and a contaminant in commercial lead.

Such soft errors, though not permanent, greatly affect the accuracy and reliability of the chip. In addition, as dimensions and operating voltages of computer chips are reduced to satisfy the demand for higher density and speed, their sensitivity to radiation increases. Thus, it is imperative that clean or "low-alpha lead" (LAL) be used in solder connections made on computer chips and circuits. As a result, it is necessary to test lead for the levels of alpha particle emission to determine whether the lead is suitable for use in electronic and computer applications.

Current methods of determining the polonium impurities in commercially available lead are time consuming, difficult, and expensive. One method involves dissolving a representative sample of the lead in acid and plating out the polonium on a metal disk. Such a method is undesirable because it is destructive, time consuming, and requires the use of caustic chemicals. Another method involves testing the polonium concentration in lead samples using a large area alpha particle detector to test a large area sample of lead. Unfortunately, the alpha particle flux only reflects the polonium impurities in the upper portion of the sample closest to the sample surface. As a result, the polonium concentration throughout the sample must be estimated based on the alpha particles detected from the surface. This can lead to an imprecise determination of polonium concentration, and in turn can lead to an imprecise prediction of alpha particle emission.

Thus, there is a need in the art for a method of preparing and testing a lead sample to determine a level of alpha particle emission which is rapid, accurate, and economical.

BRIEF SUMMARY OF THE INVENTION

The present invention relates to an improved method of preparing samples of lead for testing to determine an amount of alpha particle emission caused by naturally occurring radioactive contaminants in the lead, such as polonium. The method involves first obtaining a very thin slice from a lead sample. Next, the slices are flattened to remove any wrinkles caused by obtaining the slice, and possibly to increase the surface area of the sample slice. The flattened slices are then heated to a temperature that facilitates polonium percolation to the top and bottom surfaces of the sample slices. Finally, the lead slices are tested to determine an amount of alpha particles emitted from the slices.

BRIEF DESCRIPTION OF THE DRAWINGS

FIGS. 3A–3C is graph depicting alpha particle counts of lead samples before and after the lead samples have been treated according to the present invention.

DETAILED DESCRIPTION

Figure 1:
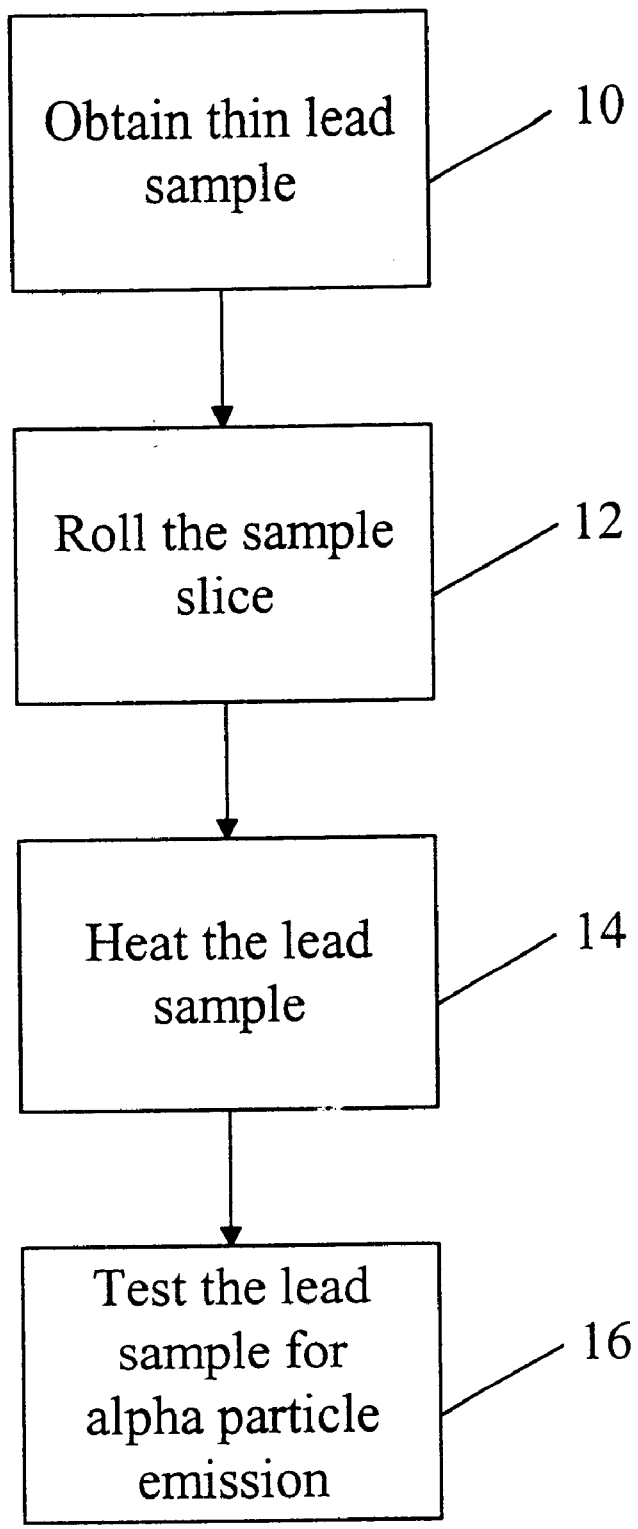
FIG. 1 is a flow diagram illustrating a method of testing lead samples for alpha particle emissions.

FIG. 1 is a flow diagram illustrating a method of testing a lead sample to determine the level of alpha particle emission caused by polonium 210 present in the lead. The first step 10 is to obtain a thin lead sample from a lead source. Obtaining a thin lead sample allows the radioactive polonium, which is the source of high energy alpha particles, to be accessible to an alpha particle detector. The thin sample allows more of the polonium alpha particles to escape from the sample, which makes it possible to get a more accurate measure of the alpha particle emissions.

Alpha particles associated with polonium have a range of approximately 15 microns in lead. Thus, for a sample that is greater than about 15 microns thick, the lead has a shielding effect which prevents the alpha particles from escaping from the lead. This shielding effect makes it difficult to obtain an accurate alpha particle emission level. Obtaining thin lead samples having a thickness of less than about 15 microns increases the ability to accurately determine the level of alpha particle emission from the lead.

Another benefit of having a thin sample is that the alpha particles which are emitted from the sample surfaces of the samples are emitted in a narrow energy range. For alpha particles at the surface of the sample, the exit energy of the particles is between about 3.6 MeV to about 5.3 MeV. This narrow energy range results from the fact that as the alpha particles move through the lead, they lose energy. When the sample is thin, the impurities are closer to the surface of the sample and the alpha particles that are emitted from the impurities must penetrate less lead before they are emitted from the lead. As a result, the alpha particles undergo less energy degradation and the resulting alpha particle emission detected is in a narrower energy range. In contrast, the energy range of alpha particles from a thicker sample have degraded energies resulting in particles with energies spread over a larger energy range, for instance from 5.3 MeV to as low as nearly 0 MeV.

Thin samples also improve the ability to detect alpha particles emitted from the lead (signal) in the presence of natural background radiation (noise). The source of background radiation is cosmic rays from solar radiation (psuedo alpha particles). The background may be higher than radiatino from the sample over the energy interval 0.0 to 10.0 MeV. Thus, surfacing the Polonium-210 on the lead will increase the number of alpha particle counts and therefore improve counting quality, i.e. the signal to noise ratio.

When obtaining a thin sample from the lead source, it is desired to obtain a very thin slice of lead, approximately five to ten microns thick. If a sample having a thickness of less than five microns is attempted, the lead tends to fall apart and crumble, resulting in an unsuitable sample. If the sample is greater than ten microns thick, the alpha particles may remain absorbed in the lead and fail to escape as desired, making it more difficult to accurately determine the alpha particle emission from the lead sample.

The thin sample may be obtained using any suitable method that yields a sample having the desired thinness. One suitable method of obtaining a sample having the desired thinness is to use a microtome to cut a slice from the lead source. Microtomes are standard equipment for the preparation of hystological slides in biology and medical laboratories, and are thus readily available. The lead source may be provided in a variety of forms, such as in pellets, blocks, or ingots. When using a microtome, it is preferable that the lead source be small enough to fit under the blade of the microtome. The shape of the ingot must also be such that the ingot can be secured, such as by using a vice, during the cutting operation of the microtome. As such, an ingot having a circular or rectangular shape is preferred when using a microtome to obtain the sample slices.

It may also be possible to obtain a thin sample slice by cutting a slice of lead using a turning lathe. However, when using a lathe the resulting slices are typically thicker and have a smaller area, both of which lessen the suitability of the resulting slices for the present method of determining polonium concentration in lead.

Slicing the lead into thin sample slices has the additional benefit of producing fractures and strains in the surface of the sample slice. Such fractures and strains further facilitate diffusion of the polonium to the surface of the sample slice. This in turn leads to a more accurate measure of the alpha particle emission.

When cutting the sample slice using a microtome, an optional second step 12 is to roll the sample slice. After cutting the slice, particularly when using a microtome, the resulting sample slice typically is wrinkled and misshaped. To obtain a better alpha particle emission reading from the sample, the sample slice is rolled to flatten out any such wrinkles. Flattening the sample slices also reduces the shielding effect of the lead that may occur in portions of the slice having a greater thickness than other portions due to the wrinkles caused by slicing the lead.

Rolling out the sample slice also ensures a more uniform surface area. This in turn maximizes the area to which the alpha particle emission detector can be exposed. Preferably, the sample slices have a surface area greater than about 15 square centimeters.

One method for rolling the sample slice is to use a rolling mill of the type used in the jewelry making industry. To ensure the sample slice does not stick to the rollers of the rolling mill, a lubricant may be used. One suitable lubricant is methanol. The rollers can be sprayed with methanol, the sample slice placed on the roller, and the sample likewise sprayed with methanol. The pressure of the rolling mill can be adjusted as desired to ensure that as the sample slice passes through the rolling mill, any wrinkles are flattened out. This process may be repeated as necessary by increasing the pressure of the rolling mill until the sample slice obtains the desired amount of smoothness.

In addition to merely flattening the sample slice, it may be possible to roll the slice in such a manner as to further decrease its thickness. One method of doing so involves increasing the pressure of the rolling mill so that not only are the wrinkles in the sample slice removed, but also the sample slice is deformed to reduce the thinness of the sample.

The thin slice is very fragile and must be handled carefully to prevent damage to the slice and prevent external contamination of its surface. Once cut, the slices may be collected in a petri dish and handled using a tweezers. Once the sample slices have been rolled to the desired smoothness, they may be removed from the rolling mill and placed on a filter paper. Using a tweezers to handle the sample slices and placing the samples on filter paper helps reduce the likelihood of contaminants being introduced onto the surface of the sample, such as skin oils, which may affect the accuracy of the alpha particle emission test. Also, because the sample slices are so thin, the filter paper is more rigid than the sample slice so that the filter paper supports the sample slices, making them easier to handle.

After rolling, the sample slice can be sized and shaped, such as by stamping or cutting the sample slice to obtain a uniform shape of all sample slices. Ensuring the sample slices are all the same size and shape allows for a better measurement of the area of each sample slice. Once sized, the sample slice may be weighed. The area of the slice and its mass can in turn be used to determine the thickness of the sample slice.

In the next step 14, the sample slice is placed on a heating rack to be heated. Heating the sample slices results in the polonium diffusing to the surface of the lead slice. By driving the polonium to the surface of the lead slice, a more accurate reading of the alpha particle emission from the sample can be obtained. When heating the sample slices, it is possible to heat several slices at a time by arranging several slices on one heating rack.

To heat the sample slices, the slices are placed in a furnace, such as a vacuum furnace or a flowing gas furnace. A vacuum furnace or flowing gas furnace is preferred to reduce external contamination or oxidation which may occur on the surface of the sample slices. Oxidation on the surface of the sample slices will impede the ability of the alpha particles to escape from the lead.

The sample slices are heated to a temperature and for a length of time which ensures that the polonium is driven to the surface of the sample slice, but is not allowed to totally diffuse out of the sample. As such, the temperature to which the sample slices are heated is close to the melting point of lead, which is 327.5° C. Preferably, the sample slices are heated to about 325° C. for about one hour. After heating the sample slices, the temperature of the furnace is cooled to less than 100° C. and the furnace is filled with an inert gas, such as nitrogen ($N_2$). The nitrogen is very dry, and prevents water vapor from forming in the furnace. The sample slices can then be removed from the oven.

The final step 16 is to test the slices to determine the amount of alpha particles being emitted from each sample slice. The amount of alpha particles being emitted may be determined using a suitable alpha particle detector, such as a Frisch Grid detector or a low background, large sample area detector. When using an alpha particle detector, the detector is first calibrated for time dependent polonium surface activity. One way to calibrate the detector is to obtain a trace standardized sample having a known polonium concentration and test the sample at a predetermined energy level. Such certified radioactive standards are commercially available from the National Institute on Standards and Technology (NIST).

After calibrating the detector, a level of background alpha particle levels in the detector chamber is determined by performing a count in an empty chamber at the same predetermined energy level as that used when testing the known sample. Once the detector is calibrated and a background level of alpha particles is determined, the samples are placed in the detector.

When placing the thin slices in the alpha particle detector, the sample slices are arranged in a manner so that the number of slices exposed to the alpha particle detector is maximized. Maximizing the number and thus cumulative surface area of the sample slices exposed to the alpha particle detector should result in a more accurate alpha particle emission count. In particular, it is desired that the cumulative sample surface area be large enough to render an alpha particle emission count greater than the background count of alpha particles in the chamber.

When obtaining the alpha particle emission levels, a top side of the slices is measured first. Once a count is collected from the top side of the slices, the slices are flipped so that an alpha particle emission level can be obtained from the bottom of the slices. The net alpha counts are determined over an appropriate counting interval. In addition, it is preferred that the counting interval be long enough so that a statistically significant level of alpha particles is detected. One appropriate counting interval is the time it takes for the sample counts to be twice that of the background counts.

The counting interval may vary based on the level of contamination in the sample slices. For instance in a sample having a high contamination level, a statistically significant count may be obtained in a shorter counting interval. In contrast, in a sample having a low contamination level, the counting interval may be much longer.

Once the initial count is obtained, it is possible to conduct another alpha particle emission test after a predetermined amount of time has passed, for instance 24 hours. The second count can be used to determine whether and how the amount of alpha particle emissions vary over time.

Table 1 below illustrated how alpha particle counts collected from a lead sample can vary over time.

TABLE 1

| | | Energy in MeV | | | |
|---|---|---|---|---|---|
| Day | Surface | 3.0–4.0 | 4.0–4.95 | 4.95–5.0 | 3.0–5.38 |
| Untreated | | | | | |
| 7 | Top | 137 | 295 | 111 | 543 |
| Treated | | | | | |
| 12 | Top | 195 | 240 | 206 | 641 |
| 16 | Bottom | 169 | 258 | 249 | 676 |
| 42 | Top | 88 | 236 | 93 | 417 |
| 48 | Bottom | 104 | 231 | 144 | 479 |

Table 1 illustrates the alpha particle emissions observed for an untreated sample and a treated sample. The treated and untreated samples comprise sample slices having a thickness of 6 microns. The time of the data collection was spread over several days to observe the movement of the polonium through the samples. As can be seen from Table 1, the alpha particle counts were taken at three ranges of energy levels, with the last row of the table indicating the total alpha particle count for all energy levels. The untreated sample was measured once at Day 7. The top of the treated sample was measured twice, at day 12 and at day 42. The bottom of the sample was measured twice as well, at day 16 and day 48.

Figure 2:
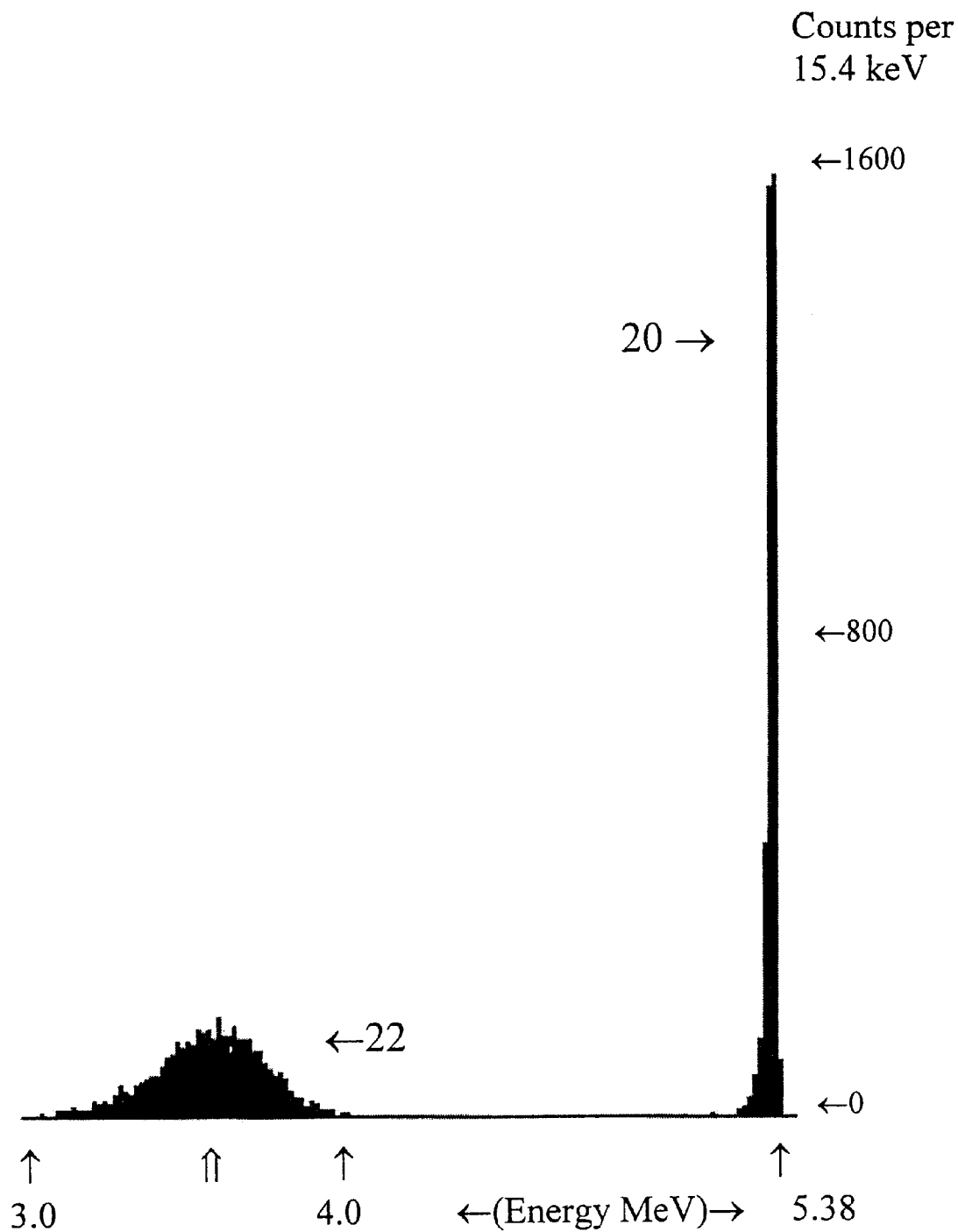
FIG. 2 is a graph depicting the results of an open and a shielded alpha particle count.

As mentioned above, it is desired to obtain alpha particle counts at a narrow energy level. FIGS. 2–3C illustrate that one desired energy range over which to test for alpha particle emissions is between about 3.0 MeV to about 5.38 MeV.

FIG. 2 is a graphical depiction of two alpha particle emission measurements taken from a collimated polonium 210 source (56 Bq). Shown on the X axis is the energy in million electron-volts (MeV). Shown on the Y-axis are the alpha particle counts per 15.4 kilo electron-volts (KeV). Two 300 second acquisitions are shown 20, 22.

The first curve 20 is indicates the particle counts per 15.4 KeV for an open source, Full Width at Half Maximum (FWHM) 26 keV, with a centroid at 5.3 MeV and an area of 3979 plus or minus 63 counts. The open source comprises polonium 210 plated on to silver. With the polonium 210 plated on silver, there is no shielding effect and all the alpha particles can easily leave the sample and be detected by the detector. As a result, the curve 20 of the open source is in the form of a spike, because the alpha particle emission is maximized and occurs in a narrow energy range.

In contrast, the second curve 22 indicates the particle counts for a shielded source, FWHM 360 keV, with a centroid at 3.6 MeV an area of 3719 plus or minus 77 counts. The shielded source comprises a polonium 210 sample having a slice of lead six microns thick placed on top of the sample during the count to simulate the shielding effect of lead. The shielding effect of the lead results in the peak shifting to a lower energy and rather than a sharp spike, the counts are in the form of a broadened curve. As can be seen from curve 22, the energy degradation of 5.3 MeV alpha particles from the bottom of a 6 micron thick lead sample is approximately 1.7 MeV (centroid at 3.6 MeV).

FIGS. 3A–3C are graphical depictions of alpha particle counts from a 6 micron thick lead sample. In FIGS. 3A–3C, the X axis the exit energy of the alpha particles in million electron-volts (MeV). The Y-axis is the alpha particle counts per 8.6 keV. FIG. 3A shows the alpha particle counts measured just after the sample has been cut and before treating. FIGS. 3B and 3C show the alpha particle counts measured after treating the slices according to the present invention. FIG. 3B shows the alpha particle counts collected when the top surface of the slice is toward the detector, and FIG. 3C shows the alpha particle counts collected when the bottom surface of the slice is toward the detector. The acquisition time for each test was 345,600 seconds (four days).

FIGS. 3B and 3C both have a spike near 5.38 MeV. This spike indicates that there are many alpha particles escaping the lead sample with little energy attenuation. FIGS. 2–3C reinforce the goals of the invention, that it is possible to use the inventive process to drive the polonium in the sample slices to the surfaces of the samples to provide for more accurate detection of emission levels. In addition, it is desirable to maintain the alpha particle emissions in a narrow energy range because the emissions can more easily be distinguished from background levels.

Although the present invention has been described with reference to preferred embodiments, workers skilled in the art will recognize that changes may be made in form and detail without departing from the spirit and scope of the invention.

What is claimed is:

1. A method of preparing a lead source for testing an amount of alpha particle emission, the method comprising:
    forming a sample from the lead source having a thinness which is conducive to alpha particle emission from the sample; and heating the sample to cause a migration of alpha particles in the sample to a surface of the sample.

2. The method of claim 1 wherein forming the sample comprises forming a sample having a thickness of between about 5 and about 10 micrometers.

3. The method of claim 1 wherein forming the sample comprises forming a sample having an area of at least about 15 square centimeters.

4. The method of claim 1 wherein forming the sample comprises cutting a sample slice from the lead source using a microtome.

5. The method of claim 4 and further comprising rolling the sample slice after cutting to flatten the sample slice.

6. The method of claim 1 wherein forming the sample comprises forming a sample having a thinness allowing alpha particle emission in an energy range of between about 3.6 million electron-volts to about 5.3 million electron-volts.

7. The method of claim 1 wherein heating the sample comprises heating the sample to about a melting point of lead.

8. The method of claim 1 wherein heating the sample comprises heating the sample to about 325° C. for about an hour.

9. The method of claim 1 wherein heating the sample comprises heating the sample to a temperature and for an amount of time that allows polonium present in the lead to dissipate toward the surface of the sample.

10. The method of claim 1 and wherein heating the sample comprises preventing surface contamination from forming on the sample.

11. A method of preparing thin lead samples for testing to determine an amount of alpha particle emissions, the method comprising:

slicing a lead sample to obtain a sample slice;

flattening the sample slice; and heating the sample slice to drive impurities to a surface of the sample slice.

12. The method of claim 11 wherein slicing a lead sample comprises using a microtome to obtain a sample slice between about 5 microns and 10 microns thick.

13. The method of claim 11 and further comprising cutting the sample slice to obtain a desired shape.

14. The method of claim 11 wherein flattening the sample slice further comprises increasing the surface area of the sample slice.

15. The method of claim 11 wherein heating the sample slice comprises heating the sample slice to about 325° C. for an hour.

16. The method of claim 11 wherein heating the sample slice further comprises preventing surface oxidation on the sample slice.

17. The method of claim 11 wherein heating the sample slice comprises heating the sample slice to about a melting point of lead.

18. The method of claim 11 and further comprising cooling the sample slice to ambient temperature in nitrogen gas.

19. A method of determining an amount of alpha particle emission from polonium atoms in a lead source, the method comprising:

obtaining a sample from the lead source having a thinness of less than about 15 microns;

heating the sample to cause a migration of polonium atoms to a surface of the sample; and testing the sample to determine an alpha particle emission level.

20. The method of claim 19 wherein obtaining the sample further comprises cutting the lead source to obtain a thin slice between about 5 microns thick and about 10 microns thick.

21. The method of claim 20 wherein obtaining the sample from the lead source comprises slicing the lead source using a microtome.

22. The method of claim 21 and further comprising rolling the sample in a rolling mill.

23. The method of claim 22 wherein rolling the sample further comprises using a lubricant to prevent the sample from sticking to the rolling mill.

24. The method of claim 22 wherein rolling the sample further serves to increase the surface area of the sample.

25. The method of claim 22 and further comprising sizing the sample slice.

26. The method of claim 19 wherein heating the sample comprises heating the sample to a temperature of about 325° C. for about an hour.

27. The method of claim 19 wherein heating the sample comprises heating the sample long enough to cause the contaminants to move to the surface of the sample but not dissipate.

28. The method of claim 19 wherein heating the sample comprises heating the sample to near the melting point of lead.

29. The method of claim 19 wherein heating the sample further comprises preventing surface oxidation.

30. The method of claim 19 wherein testing the sample to determine an alpha particle emission level comprises using a Frish grid detector.

31. The method of claim 19 wherein testing the sample to determine an alpha particle emission level comprises using a low background, large sample area detector.

* * * * *